US006167311A

United States Patent [19]
Rezai

[11] Patent Number: 6,167,311
[45] Date of Patent: Dec. 26, 2000

[54] METHOD OF TREATING PSYCHOLOGICAL DISORDERS BY BRAIN STIMULATION WITHIN THE THALAMUS

[75] Inventor: Ali R. Rezai, New York City, N.Y.

[73] Assignee: Electro Core Techniques, LLC, Summit, N.J.

[21] Appl. No.: 09/332,806

[22] Filed: Jun. 14, 1999

[51] Int. Cl.$^7$ .................................................. A61N 1/36
[52] U.S. Cl. .............................................................. 607/45
[58] Field of Search ............................... 607/45; 600/378, 600/544

[56] References Cited

U.S. PATENT DOCUMENTS

| | | | |
|---|---|---|---|
| 5,299,569 | 4/1994 | Wernicke et al. | 607/45 |
| 5,938,688 | 8/1999 | Schiff | 607/45 |

*Primary Examiner*—Scott M. Getzow
*Attorney, Agent, or Firm*—Joseph P. Errico, Esq.

[57] ABSTRACT

A method for treating psychological disorders such as obsessive compulsive disorder, Tourette's syndrome, depression, bipolar disorder, panic attacks, schizophrenia, and attention deficit disorder by stimulation of the thalamus, and in particular regions within the anterior and intralaminar nuclei of the thalamus. The method includes the steps of determining a common group of patients, each suffering from a common specific diagnosis for a psychological disorder; determining which common region of the patients' thalami are involved in carrying the pathological electrical signals which may otherwise be generated in dissimilar and disparate regions of the brains of the patients; surgically implanting an electrode and electrical signal generating device such that the electrode is positioned within the region of the thalamus identified as the common nexus; and selectively adjusting the level of electrical stimulation in accordance with the specific effect of the stimulation of the patient. In particular, the regions of the thalamus most frequently associated with psychological disorders are the anterior and intralaminar nuclei.

29 Claims, 2 Drawing Sheets

METHOD OF TREATING PSYCHOLOGICAL DISORDERS BY BRAIN STIMULATION WITHIN THE THALAMUS

BACKGROUND OF THE INVENTION

1. Field of the Invention

This invention relates generally to the treatment of psychological disorders by stimulating appropriate regions of the thalamus, and more particularly to a method of interrupting pathological electrical activity of the brain by electrical stimulation of the corresponding nucleus or nuclei of the thalamus, and most specifically to the stimulation of the central median nuclei, intralaminar nuclei, and/or the central lateral nuclei.

2. Description of the Prior Art

Within the field of neurosurgery, the use of electrical stimulation for treating pathologies, including such disorders as compulsive eating, chronic pain, and movement disorders, such as Parkinson's disease essential tremor, has been widely discussed in the literature. It has been recognized that electrical stimulation holds significant advantages over alternative methods of treatment, for example lesioning, inasmuch as lesioning can only destroy nerve activity. In many instances, the preferred effect is to stimulate or reversibly block nervous tissue. Electrical stimulation permits such stimulation of the target neural structures, and equally importantly, it does not require the destruction of the nervous tissue (it is a reversible process, which can literally be shut off or removed at will).

Within this field, however, disorders manifesting gross physical dysfunction, not otherwise determinable as having emotional or psychiatric origins, comprise the vast majority of those pathologies treated by deep brain stimulation. A noteworthy example of treatment of a gross physical disorder by electrical stimulation is included in the work of Alim Benabid, and his research team, who have proposed a method of reducing, and in some cases eliminating, the temor associated with Parkinson's disease by the application of a high frequency electrical pulse directly to the subthalamic nucleus (see Neurosurgical Operative Atlas, Vol. 8, March 1999, pp. 195–207, Chronic Subthalamic Nucleus Stimulation For Parkinson's Disease; and New England Journal of Medicine, Vol. 339, October 1998, pp. 105–1111, Electrical Stimulation of the Subthalamic Nucleus in Advanced Parkinson's Disease).

Conversely, direct neuro-augmentation treatments for disorders which have traditionally been treated by behavioral therapy or psychiatric drugs, has been largely limited to peripheral nerve stimulation. A noteworthy example is the effort to control compulsive eating disorders by stimulation of the vagus nerve which has been described by Wernicke, et al. in U.S. Pat. No. 5,263,480. This treatment seeks to induce a satiety effect by stimulating the afferent vagal fibers of the stomach. For patients having weak emotional and/or psychological components to their eating disorders, this treament can be effective insofar as it eliminates the additional (quasi-normal) physio-chemical stimulus to continue eating. This is especially true for patients who exhibit subnormal independent functioning of these fibers of the vagus nerve. For compulsive eating patients who are not suffering from an insufficient level of afferent vagal nerve activity resulting from sufficient food intake, however, the over stimulation of the vagus nerve and potential resultant over abundance of satiety mediating chemicals (cholecystokinin and pancreatic glucagon) may have little effect. It has even been suggested that continued compulsive eating, despite overstimulation of the vagus nerve, may exacerbate the emotional component of the patient's disorder. This, therefore, begs the question, is vagus nerve stimulation useful in treating the psychological component of the disorder of compulsive eating, or is it simply a method of minimizing the additional, but natural, pressures to eat because of normal physical hunger. More generally, the question may be asked, is peripheral nerve stimulation of any kind the most appropriate method of treatment for disorders which are, at the core, the result of a pathology exhibited in the brain.

If the answer to this question is that the stimulation of a peripheral nerve can result in the release of a chemical which specifically counteracts the psychological pathology, for example if the release of greater amounts of cholecystokinin and pancreatic glucagon had a direct effect on the pathology exhibited in the brain, then, for that patient, the treatment will have a greater probability of success. If, however, as is most probably the case, the increase in the level of activity of the peripheral nerve does not result in the release of such a chemical, and therefore, has no effect on the area of the brain responsible for the emotional/psychiatric component of the disorder, then the treatment will have a much lower probability of success.

The impetus would, therefore, be to treat psychological disorders with direct modulation of activity in that portion of the brain which is causing the pathological behavior. Unfortunately, the ability to determine what region of the brain is responsible for a given patient's disorder is very difficult, and even more importantly, does not usually provide consistent patterns across a population of similarly afflicted patients. By this it is meant that the region of the brain which causes the behavioral pathology of one compulsive eating patient, for example, does not necessarily correspond in any way with the region of another compulsive eating patient.

In some manner, however, the determination of what regions of the brain are exhibiting pathological function must be determined. Fortunately, a method for determining precisely this has been developed by a number of researchers. Normal brain function can be characterized by four discrete frequencies of electrical output. Other frequencies are almost exclusively associated with pathology. The use of magnetoencephalography (MEG scans) has permitted quantificaion of electrical activity in specific regions of the brain. It has been proposed that MEG scans may be used to identify regions exhibiting pathological electrical activity. The resolution of the MEG scans of the brain are highly accurate (sub-one millimeter accuracy), however, correlating the MEG scan with MRI images for the surgical purposes of identifying anatomical structures limits the overall resolution for surgical purposes to a volume of 10 to 30 cubic millimeters. As stated above, however, simply identifying the regions of the brain which are exhibiting pathological electrical activity for a specific patient is not sufficient to generalize across a large population of patients, even if they are exhibiting identical disorders.

Fortunately, the architecture of the brain provides a substantial advantage in the search for a generic solution. This design advantage takes the form of a centralized signalling nexus through which many of the brain's disparate functions are channeled in an organized and predictable manner. More particularly, the thalamus is comprised of a large plurality (as many as one hundred, or more) of nerve bundles, or nuclei, which receives and channels nerve activity from all areas of the nervous system and interconnects various activities within the brain. The thalamus has been metaphorically described by some as the brain's equivalent of a highly organized train station. Many different train tracks come together, and many trains carrying many different cargos enter, however, if one has a schedule and a map, it is easy to find all the trains which carry coal (whether from Pennsylvania, West Virginia, Tennessee, or Arkansas), because all coal carriers are routed through the same tracks. It is this key which permits the treatment of common psychological disorders by brain stimulation of one specific area, rather than having to customize the (gross) placement of the stimulator for each patient.

It is therefore the principal object of the present invention to provide a more generically applicable method for treating certain psychological disorders.

It is further an object of the present invention to provide a fully reversible and adjustable method of treating certain psychological disorders.

It is still further an object of the present invention to provide a method of treating certain psychological disorders the effectiveness of which may be evaluated rapidly.

It is also an object of the present invention to provide a method of interventionally treating certain psychological disorders while minimizing the necessary pathological investigaion.

SUMMARY OF THE INVENTION

The preceding objects are provided in the present invention, which comprises new and novel methods of treating psychological disorders by implantation of stimulation electrodes at specific locations in the thalamus. In another aspect, the present invention also comprises new and novel methods for identifying the proper positioning of the electrodes within the thalamus for a given specific psychological disorder. More particularly, in the first aspect, the present invention comprises a method of therapeutically treating a psychological disorder by surgically implanting an electrode into a predetermined site within the brain of the patient, wherein the predetermined site is selected from the group of non-specific nuclei residing within the intralaminar nuclei or anterior thalamic nuclei. Referring more particularly to FIG. 1, the anterior thalamic nuclei 100 are located in the most anterior portion of the thalamus and are interconnected with the frontal lobes. The intralaminar nuclei 102 have more diffuse projections. Together these nuclei groups are the most likely associated with psychological disorders. The intralaminar nuclei 102 are located in the paramedian thalamus (dividing each of the lobes of the thalamus along a Y shaped vertical planar geometry which cuts through the posterior to anterior axis of each lobe). Referring now to FIG. 2, within the intralaminar group 102 are principally the anterior 104, midline 106, and posterior 108 subgroups. The anterior subgroups 104 include the central lateral (CL) and paracentralis regions. The posterior subgroups 108 include the centromedian-parafascicularis complex (Cm-Pf). The midline 106 and other related subgroups include the centre medial (CeM) nuclei and paraventricularis (Pv).

The anterior thalamic nuclei are coupled most directly to the frontal lobes which are most associated with personality and behavior. The posterior subgroup of the intralaminar nuclei, including the centromedian-parafascicularis, is coupled most directly to the prefrontal, permotor, and parietal cortices. The anterior subgroup, including the central lateral and paracentralis nuclei, is most directly connected to the parietal, visual association, prefrontal, frontal, and superior temporal cortices as well as the frontal eye field. The midline and related intralaminar subgroups, including the paraventricularis, centre medial, midline nuclei, are connected to the orbital frontal cortex, the hippocampus, the limbic cortex, and the amygdala.

In the first aspect of the invention, therefore, the proximal end of the electrode is coupled to an electrical signal source which, in turn, is operated to stimulate the predetermined treatment site in the thalamus of the brain, such that the clinical effects of the psychological disorder are reduced.

In the second aspect, the present invention comprises a method of determining the proper therapeutic treatment, i.e., the proper position or placement of the electrodes, for a specific psychological disorder comprising the steps of identifying a large sampling of patients, each exhibiting a common specific psychological disorder and then identifying which common region or nuclei of their thalamuses exhibits pathological electrical activity during manifestations of the specific psychological disorder. The common regions demonstrating this pathological activity constitute the predetermined treatment site, whereafter a suitable means for affecting the activity of said predetermined treatment site may be employed to ameliorate the psychological disorder generically with a high probability of success.

In particular, the regions identified above, including the anterior and intralaminar nuclei, are herein identified by their known anatomical connections and functional brain imaging as being actively involved in channeling or gating the pathological electrical activity associated with psychological disorders. It is important to note that these regions, their functions, and their connections are common structural features of human brains, and therefore are common targets across a large number of patients. As suggested above, this commonality of function and structure within the thalamus allows for common treatment targeting, even in instances wherein different patients have other disparate locations within their brains which also exhibit pathological electrical activity.

DETAILED DESCRIPTION OF THE PREFERRED EMBODIMENT

Figure 1:
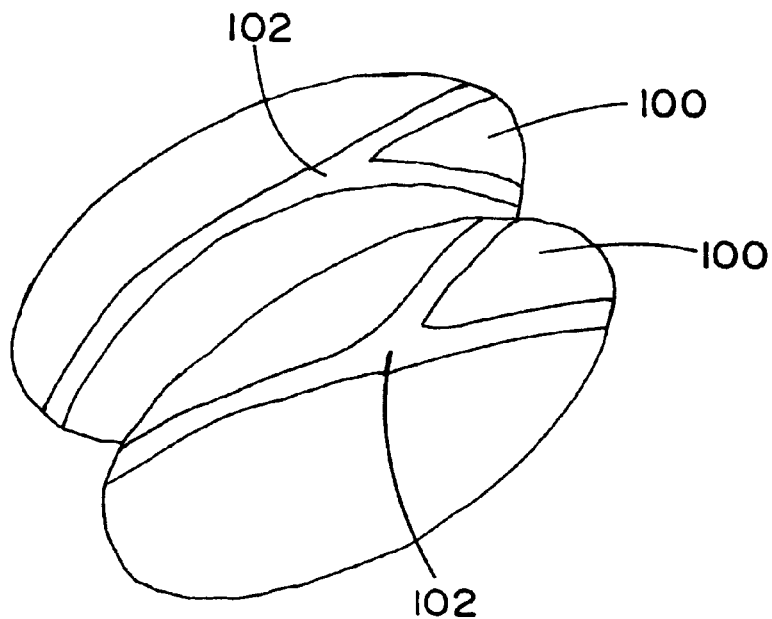
FIG. 1 is a perspective view of a human thalamus, having various regions thereof outlined.
Figure 2:
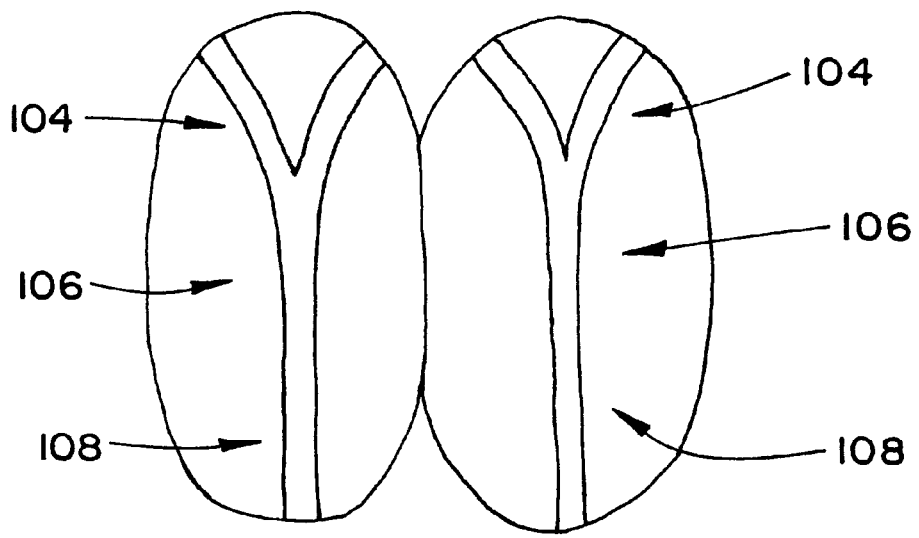
FIG. 2 is a schematic top view of the human thalamus, again having various regions thereof outlined.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

The present invention comprises a method of identifying and treating patients who suffer from certain known psychological disorders. As suggested by this introductory statement, the specific steps involved with this method comprise two separate stages: first, the identification of patients and the preparation for surgical intervention; and second, the actual surgical procedure.

With respect to the first of these stages, that is the pre-operative steps, the identification of suitable patients begins with the accumulation of physical, chemical, and historical behavioral data on each patient. A collection of patients who have been identified as exhibiting similar clinical symptoms are then grouped together and subject to a series of common non-invasive brain imaging studies. These brain imaging studies are intended to identify the regions of the brain, and more particularly, the regions of the thalamus, which exhibit clinically recognizable deviation from normal electrical activity. Several diagnostic tools are useful in this capacity, including fluoro-deoxyglucose-positron-emission tomography (FDG-PET), electro-encephalography (EEG), magnetic resonance imaging (MRI), and most importantly, magnetoencephelagraphy.

A magnetoencephalograph (MEG) is a device which utilizes a plurality of spatially distributed, highly sensitive, superconducting circuits to register the electrical activity of the brain. The circuits can measure the frequency of the activity at different points in the brain by correlating the interferences registered in each superconducting circuit. As the normal frequencies of brain activity are known, and specific frequency ranges associated with neural dysfunction have been reported, it is possible to identify the specific regions of the brain exhibiting neural dysfunction.

The correlation of specific areas of the brain which are not demonstrating nomal activity across a group of patients exhibiting similar clinical symptoms and who are similarly diagnosed is not assumed a priori. The nature of the brain's architecture provides a substantial advantage in this arena. The brain channels nearly all of its signalling activity through the thalamus. In an organized fashion, similar peripheral activity, i.e. activity in the peripheral areas of the brain which are associated with the same, or similar conditions, are channeled through the same areas of the thalamus. In this way, the thalamus acts as a train switching station, or as a post office, rerouting disparate signals along similar paths when the appropriate outcomes of the original signals are similar. This effect is nowhere more impresive than in the examples presently being illustrated. For example, two patients exhibiting similar clinical conditions, for example physical motion tics associated with florid Tourette's syndrome, may have very different peripheral brain dysfunction, but probably channel the abnormal electrical signals through the same nucleus within the thalamus.

The precise mapping of this abnormal signalling, however, is not possible solely by using the MEG. While the use of the MEG is a substantial advantage in determining whether disparate abnormal peripheral activity is channeled through the thalamus in a similar way, the resolution of the device does not permit pinpoint accuracy in this determination. In fact, the resolution of the MEG is substantially less sharp than the implantable electrodes which are to be used in the surgical intervention. The correlation of actual data from test implantations as well as a deep understanding of the brain's architecture is necessary to identify the specific target nuclei. Additionally, however, the instruments utilized in guiding the surgeon in placing the actual electrodes into the thalamus have a similar degree of variability, or limit of resolution. Fortunately, the state of the art in surgical intervention and the resilience of the brain tissue permits a small degree of manipulation of the electrode once it is inserted. In fact, a number of advanced electrode designs have been presented which permit the micromanipulation of each of the electrical contacts' position without macromanipulation of the overall electrode.

In the present invention, psychological disorders such as Tourette's syndrome, obsessive compulsive disorders (including individuals who exhibit extreme behavioral disfunction including excess washing, counting, checking, hoarding, or body dismorphic disorders in which individuals seek to surgically alter their appearance repeatedly because they are subject to the unwarranted belief that they are disfigured), depression, bipolar disorder, panic attacks, schizophrenia, and attention deficit disorder, are identified as having a probable commonality in thalamic activity associated with the anterior and intralaminar nuclei. Therefore, once a patient has been identified as exhibiting abnormal clinical behavior symptomatic of one of these disorders, subsequent pre-operative brain imaging scans are used to support the presumption that the abnormal signals associated with the disorder are being channelled through one of these related regions of the thalamus, and then surgical intervention with electrical stimulation is taken.

Figure 3:
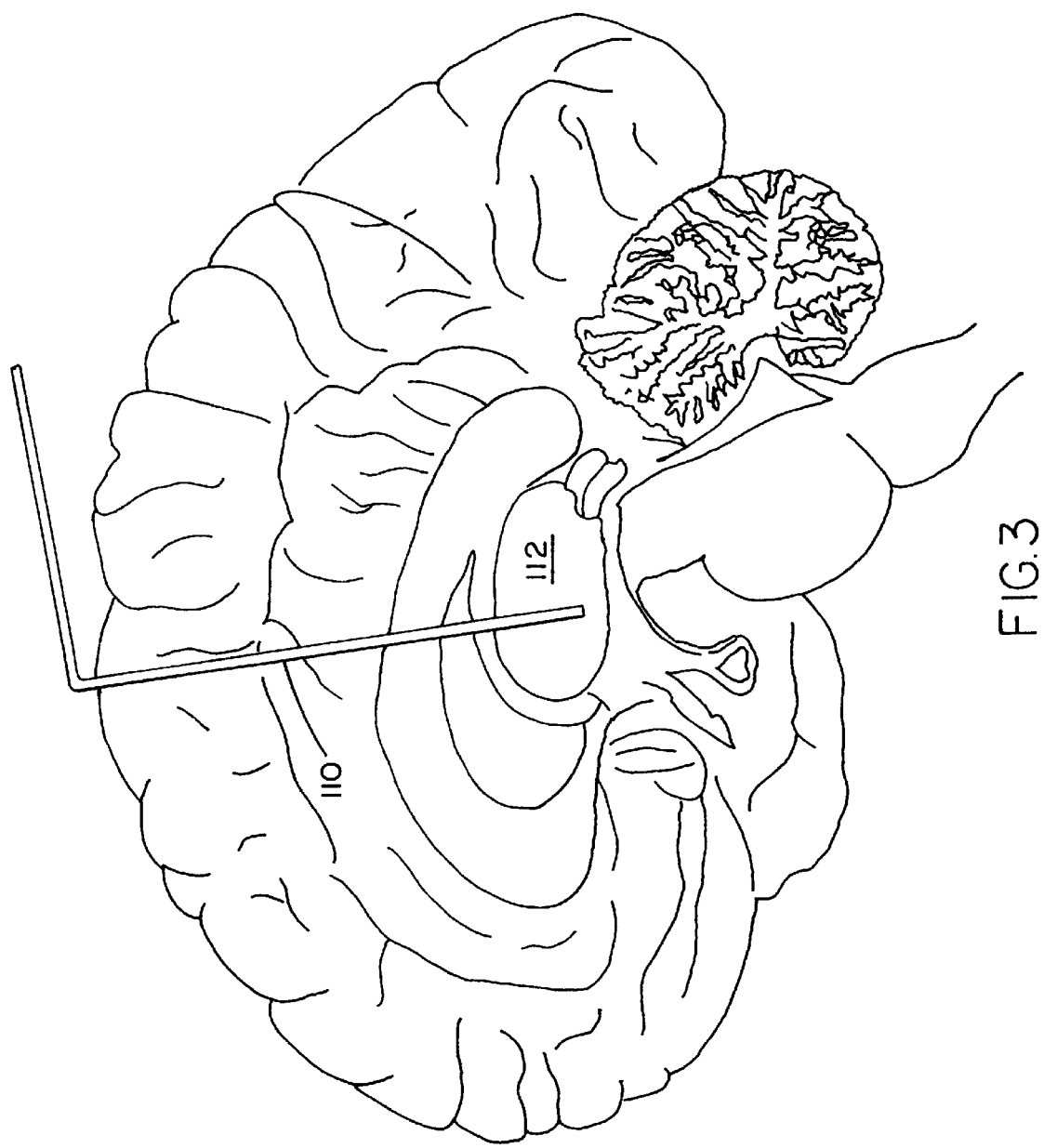
FIG. 3 is a side cross-section view of a human brain having a stimulation electrode implanted in the thalamus in acordance with a method which is an aspect of the present invention.

Surgical intervention comprises the second stage of the treatment. It is the specific use of the stimulator, for treatment of psychological disorders which comprises the inventive step in the present method, and not the implantation technique itself. More particularly, the standard neurosurgical techniques for implantation of an electrical stimulation device into the brain may be utilized. In fact, referring to FIG. 3, in which a side cross-section of a human brain having a stimulation electrode 110 implanted into the thalamus 112 (and more particularly, the intralaminar nuclei thereof) is provided, it shall be understood that the impantation of electrodes into various regions of the brain, including the thalamus is known. It is the application of this technique for the treatment of psychological disorders which has not previously been described. This technique, therefore, is as follows.

Patients who are to have an electrode implanted into the brain, first have a steroetactic head frame, such as the Leksell, CRW, or Compass, is mounted to the patient's skull by fixed screws. Subsequent to the mounting of the frame, the patient undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The head frame is therefore rigidly mounted to the sugical table. Subsequently, a series of reference points are established relative aspects of the frame and patient's skull, so that the computer can adjust and calculate the correlation between the real world of the patient's head and the virtual space model of the patient MRI scans. The surgeon is able to target any region within the stereotactic space of the brain within 1 millimeter precision. Initial anatomical target localization is achieved either directly using the MRI images, or indirectly using interactive anatomical atlas programs which map the atlas image onto the steroetactic image of the brain. In the present invention, the target space is that occupied by the anterior and intralaminar nuclei.

The surgery itself can be performed under either local or general anaesthetic. An initial incision is made in the scalp, preferably 2.5 centimeters lateral to the midline of the skull, anterior to the coronal suture. A burr hole is then drilled in the skull itself; the size of the hole being suitable to permit surgical manipulation and implantation of the electrode. This size of the hole is generally about 14 millimeters. The dura is then opened, and a fibrin glue is applied to minimize cerebral spinal fluid leaks and the entry of air into the cranial cavity. A guide tube cannula with a blunt tip is then inserted into the brain parechyma to a point approximately one centimeter from the target tissue. At this time physiological localization starts with the ultimate aim of correlating the anatomical and physiological findings to establish the final stereotactic target structure.

Physiological localization using single-cell microelectrode recording is preferable for definitive target determination. Sole reliance on anatomical localization can be problematic because of the possible discrepancies between the expected location (expected from the visualization provided by the virtual imaging of the MRI) and the actual position within the skull. Microelectrode recording povides exquisite physiological identification of neuronal firing patterns via direct measures of individual single unit neuronal acitivity. Single-cell microelectrode recordings obtained from intralaminar thalamic cells typically have a characteristic bursting activity. In addition to microelectrode recording, microstimulation and or macrostimulation may be performed to provide further physiological localization.

Once the final target nuclei have been identified in the real spatial frame of reference, the permanent electrode is implanted. General principles guiding the final implantation of the electrode involve the placement of the electrode in a region, and in an orientation, allowing for maximal efficacy while minimizing the undesired side effects. The currently used brain stimulating electrodes are quadripolar electrodes. The electrode itself is approximately 1–1.5 millimeter diameter flexible elastomeric sheath which contains four wound wire leads. The leads terminate at the distal and proximal ends of the sheath in four electrically insulated cylindrical contact pad. The contact pads at the distal end are less than 2 millimeters in length and are separated by an insulating distance, for example between 0.5 and 2 millimeters. At the proximal end, which is anywhere from 25 to 50 centimeters distance from the distal end, a corresponding series of contacts are provided so that the electrode may be coupled to a potential source, or to a coupling lead which permits remote disposition of the signal source.

The initial application of the electrical signal through the electrode is then attempted. The range of signal types are between 0.1 to 20 volts, with a pulse width of 10 microseconds to 1000 microseconds, and a frequency of 2 to 2500 Hertz. The stimulation can be monopolar or bipolar depending upon the specific relative potentials applied to the electrical contacts relative to the patient's tissue. Various stimulation parameters are tested to assess side effects (such as motor contraction, paresthesias, visual disturbance, pain, and autonomic modulation) or clinical efficacy. Psychological disorders treated by electrostimulation, however, may take up to six months to demonstrate clinical efficacy. Long term adjustment of the signal being applied by the power source may be required to optimize the outcome. If the patient's symptoms do not subside, the surgeon will attempt to adjust all of the parameters until they do.

As is readily obvious to anyone who has witnessed the unnecessary surgical procedure associated with the remote localization of the power source, it is desirable the burr cap structure itself comprise the signal source. However, as that option is not presently available the signal source generator must be disposed at a remote site in the patient's body. A specially designed plastic cap is generally provided to seat in the burr hole, and permit the proximal end of the electrode to pass out through the skull. The incision in the patient's skull is then sutured closed with the electrode temporarily stored under the skin. If the patient is not already under general anaesthesia, the patient is so disposed and a tunnel is formed under the dermal layers, connecting the incision in the scalp to the remote location for the signal generator (usually the infraclavicular region, beneath the collar bone - where cardiovascular pace makers are implanted). Subsequent joining of the electrode to a coupling (extending) lead from the signal source to the brain electrode is then necessary, however, generally the manner in which the electrode and the lead are coupled utilizes the same terminal contacts as would be used for direct coupling to the power source.

Once the sugery is complete, a non-contrast CT scan is taken to ensure that there is no intracranial hematoma. Subsequently, various stimulation parameters are programmed and patients are assessed for any side effects as well as clinical efficacy. As behavioral and related cognitive improvement may not occur immediately, long-term benefits may not be achieved until multiple adjustmnts are accomplished.

While there has been described and illustrated specific embodiments of new and novel methods of treatment for psychological disorders, it will be apparent to those skilled in the art that variations and modifications are possible without deviating from the broad spirit and principle of the present invention which shall be limited solely by the scope of the claims appended hereto.

We claim:

1. A method of therapeutically treating a psychological disorder by means of an implanted electrode coupled to an electrical signal source comprising the steps of:

surgically implanting said electrode in a brain of a patient so that a distal end thereof lies in communication with a predetermined treatment site in the thalamus of the brain, said predetermined site being selected from the group consisting of the anterior and intralaminar nuclei;

coupling a proximal end of said electrode to said electrical signal source; and operating said electrical signal source to stimulate said predetermined treatment site in the thalamus of the brain, whereby the effects of psychological disorder are reduced.

2. The method as set forth in claim 1, wherein said stimulation increases thalamic activity.

3. The method as set forth in claim 1, wherein said stimulation decreases thalamic activity.

4. The method as set forth in claim 1, wherein said step of operating said electrical signal source comprises the step of operating said electrical signal source in a high frequency range of 50 to 2500 Hz.

5. The method as set forth in claim 1, wherein said step of operating said electrical signal source comprises the stepof operating said elctrical signal source in a low frequency range of 2 to 100 Hz.

6. The method as set forth in claim 1, wherein the stimulation is applied as a monopolar stimukation.

7. The method as set forth in claim 1, wherein the stimulation is applied as a bipolar stimulation.

8. The method as set forth in claim 1, wherein the stimulation is applied as a multipolar stimulation.

9. The method as set forth in claim 1, wherein said step of operating said electrical signal source comprises the step of operating said electrical signal source with a pulse width of selected from the range of 50 to 500 microseconds.

10. The method as set forth in claim 1, wherein said step of operating said electrical signal source comprises the step of operating said electrical signal source with a voltage selected from the range of 0.1 to 20 volts.

11. The method as set forth in claim 1, wherein said psychological disorder is selected from the group consisting of Tourette's syndrome, obsessive compulsive disorder, depression, bipolar disorder, panic attacks, schizophrenia, and attention deficit disorder.

12. A method of therapeutically treating a psychological disorder by means of an implanted electrode coupled to an electrical signal source comprising the steps of:
   identifying a specific psychological disorder exhibited by a patient;
   surgically implanting said electrode in the brain of said patient so that a distal end thereof lies in communication with a predetermined treatment site in the thalamus of the brain, which predetermined treatment site is in correspondence with the common site exhibiting pathological electrical activity across a large sampling of patients exhibiting said specific psychological disorder, said predetermined site being selected from the group consisting of the the anterior and intralaminar nuclei;
   coupling a proximal end of said electrode to said electrical signal source; and
   operating said electrical signal source to stimulate said predetermined treatment site in the thalamus of the brain, whereby the effects of psychological disorder are reduced.

13. The method as set forth in claim 12, wherein said stimulation increases thalamic activity.

14. The method as set forth in claim 12, wherein said stimulation decreases thalamic activity.

15. The method as set forth in claim 12, wherein said step of operating said electrical signal source comprises the step of operating said electrical signal source in a high frequency range of 50 to 2500 Hz.

16. The method as set forth in claim 12, wherein said step of operating said electrical signal source comprises the stepof operating said elctrical signal source in a low frequency range of 2 to 100 Hz.

17. The method as set forth in claim 12, wherein the stimulation is applied as a monopolar stimukation.

18. The method as set forth in claim 12, wherein the stimulation is applied as a bipolar stimulation.

19. The method as set forth in claim 12, wherein the stimulation is applied as a multipolar stimulation.

20. The method as set forth in claim 12, wherein said step of operating said electrical signal source comprises the step of operating said electrical signal source with a pulse width of selected from the range of 50 to 500 microseconds.

21. The method as set forth in claim 12, wherein said step of operating said electrical signal source comprises the step of operating said electrical signal source with a voltage selected from the range of 0.1 to 20 volts.

22. The method as set forth in claim 12, wherein said psychological disorder is selected from the group consisting of Tourette's syndrome, obsessive compulsive disorder, depression, bipolar disorder, panic attacks, schizophrenia, and attention deficit disorder.

23. A method of determining the proper therapeutic treatment for, and subsequently treating a specific psychological disorder by means of an implanted electrode coupled to an electrical signal source comprising the steps of:
   identifying a large sampling of patients, each exhibiting a common specific psychological disorder;
   identifying which common region of the thalamus exhibits pathological electrical activity during manifestations of the specific psychological disorder, said common region thereafter constituting a predetermined treatment site;
   surgically implanting said electrode in the brain of each of said patients so that a distal end thereof lies in communication with the predetermined treatment site in the thalamus of the brain, said predetermined site being selected from the group consisting of the anterior and intralaminar nuclei;
   coupling a proximal end of said electrode to said electrical signal source; and
   operating said electrical signal source to stimulate said predetermined treatment site in the thalamus of the brain, whereby the effects of psychological disorder are reduced.

24. The method as set forth in claim 23, wherein said stimulation increases thalamic activity.

25. The method as set forth in claim 23, wherein said stimulation decreases thalamic activity.

26. The method as set forth in claim 23, wherein said psychological disorder is selected from the group consisting of Tourette's syndrome, obsessive compulsive disorder, depression, bipolar disorder, panic attacks, schizophrenia, and attention deficit disorder.

27. A method of determining the proper therapeutic treatment for a specific psychological disorder comprising the steps of:
   identifying a large sampling of patients, each exhibiting a common specific psychological disorder; and
   identifying which common region of the thalamus exhibits pathological electrical activity during manifestations of the specific psychological disorder, said common region thereafter constituting a predetermined treatment site, whereafter a suitable means for affecting the activity of said predetermined treatment site may be employed.

28. The method as set forth in claim 27, wherein the common regions of the thalamus constituting the predetermined treatment site is selected from the group consisting of the anterior and intralaminar nuclei.

29. The method as set forth in claim 27, wherein saidpsychological disorder is selected from the group consisting of Tourette's syndrome, obsessive compulsive disorder, depression, bipolar disorder, panic attacks, schizophrenia, and attention deficit disorder.

* * * * *